(12) United States Patent
Bellhouse et al.

(10) Patent No.: US 7,207,967 B1
(45) Date of Patent: Apr. 24, 2007

(54) PARTICLE DELIVERY

(75) Inventors: Brian John Bellhouse, Oxfordshire (GB); Paul Rudd Drayson, Oxfordshire (GB); John Christopher Greenford, Oxfordshire (GB); Charles David Ogilvy Potter, Oxford (GB); David Francis Sarphie, Oxfordshire (GB)

(73) Assignee: PowderJect Research Limited, Oxford (GB)

( * ) Notice: Subject to any disclaimer, the term of this patent is extended or adjusted under 35 U.S.C. 154(b) by 1339 days.

(21) Appl. No.: 08/800,016

(22) Filed: Feb. 13, 1997

Related U.S. Application Data

(63) Continuation-in-part of application No. PCT/GB95/01948, filed on Aug. 17, 1995.

(30) Foreign Application Priority Data

Aug. 17, 2004 (GB) .............................. 9416663

(51) Int. Cl.
*A61M 5/30* (2006.01)

(52) U.S. Cl. .......................... 604/70; 604/68
(58) Field of Classification Search .................. 604/68, 604/69, 70, 71, 72, 88, 131, 140, 141, 143, 604/522, 57–64, 147–148
See application file for complete search history.

(56) References Cited

U.S. PATENT DOCUMENTS

| | | | |
|---|---|---|---|
| 2,501,047 A | * | 3/1950 | Gustafsson et al. ........... 604/58 |
| 3,788,315 A | | 1/1974 | Laurens |
| 3,859,996 A | * | 1/1975 | Mizzy et al. .................. 604/70 |
| 4,017,007 A | * | 4/1977 | Riccio .......................... 604/58 |
| 4,596,556 A | | 6/1986 | Morrow et al. |
| 4,945,050 A | | 7/1990 | Sanford et al. |
| 5,062,830 A | | 11/1991 | Dunlap |
| 5,149,655 A | | 9/1992 | McCabe et al. |
| 5,204,253 A | | 4/1993 | Sanford |
| 5,256,142 A | * | 10/1993 | Colavecchio ............... 604/110 |
| 5,304,125 A | * | 4/1994 | Leith ........................... 604/58 |
| 5,371,015 A | | 12/1994 | Sanford et al. |
| 5,415,631 A | * | 5/1995 | Churinetz et al. ............ 604/58 |
| 5,630,796 A | * | 5/1997 | Bellhouse et al. ............ 604/58 |

FOREIGN PATENT DOCUMENTS

| | | |
|---|---|---|
| EP | 0 406 788 A1 | 1/1991 |
| EP | 0 535 005 B1 | 4/1993 |
| FR | 2 360 031 | 8/1978 |
| GB | 1049780 | 11/1966 |
| WO | WO 91/00915 | 1/1991 |
| WO | WO 92/04439 | 3/1992 |
| WO | WO 95/19799 | 7/1995 |
| WO | WO 96/04947 | 2/1996 |

* cited by examiner

*Primary Examiner*—Manuel Mendez
(74) *Attorney, Agent, or Firm*—Foley & Lardner

(57) ABSTRACT

A needleless syringe particle delivery system is provided. The needleless syringe has an elongate nozzle that is connected at its upstream end to a sealed chamber. The sealed chamber contains gas at super-atmospheric pressure and particles of a therapeutic agent. Upon release of the gas from the sealed chamber, a flow is formed which entrains the particles and allows the particles to pass through the nozzle at supersonic speed for subsequent delivery to a target surface.

27 Claims, 8 Drawing Sheets

Fig.1.
Fig.2.
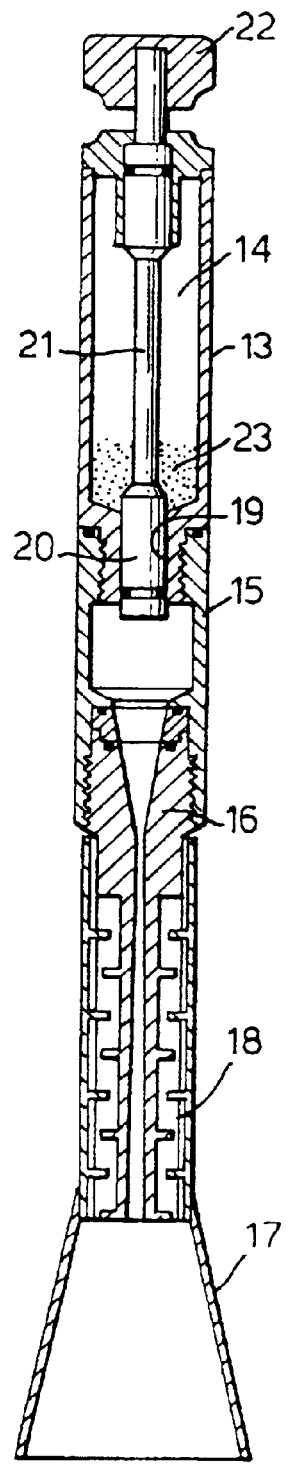
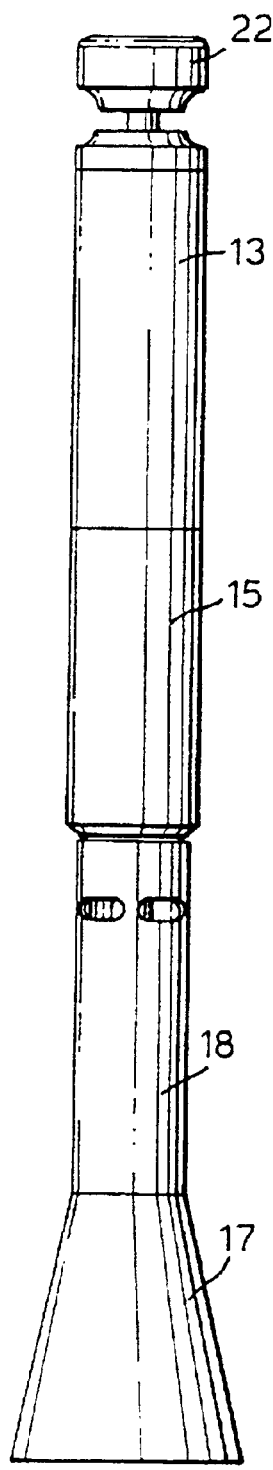

Fig.5.
Fig.6.
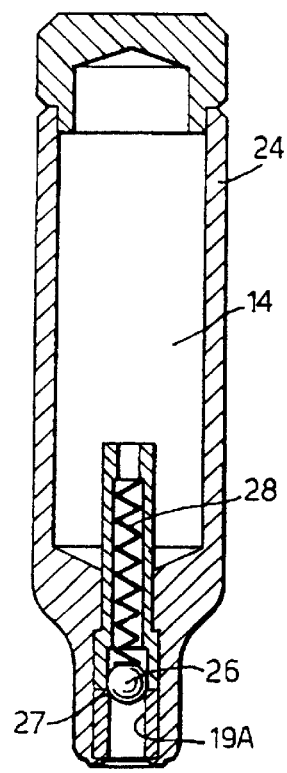
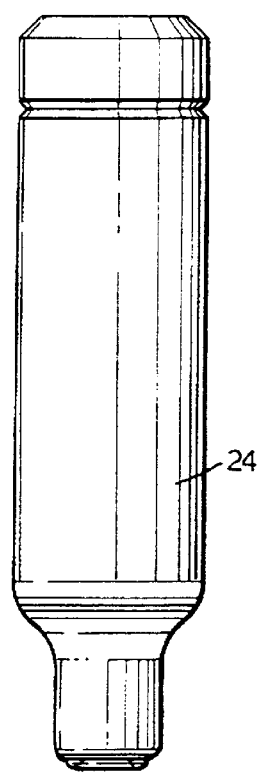
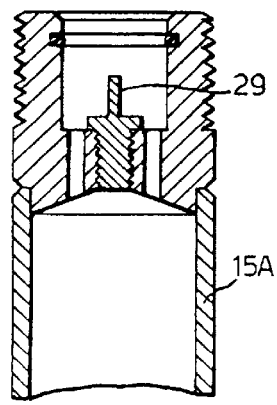
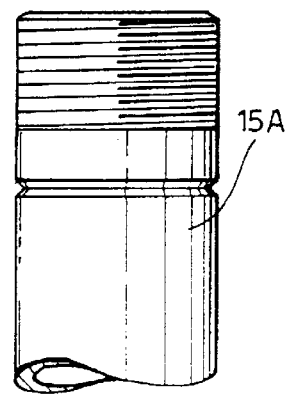

Fig.7.
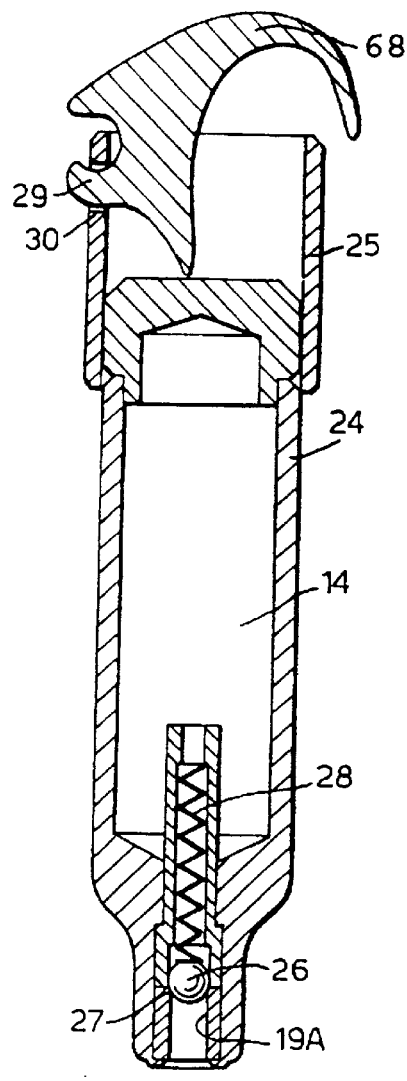
Fig.8.
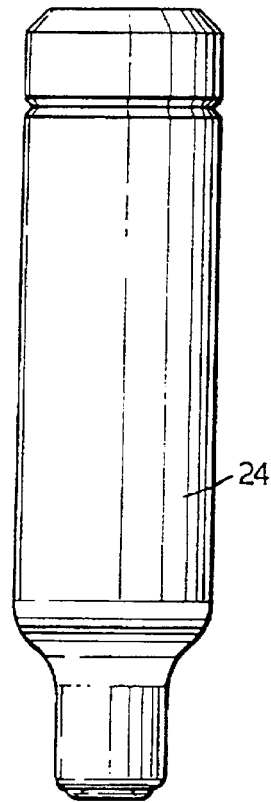
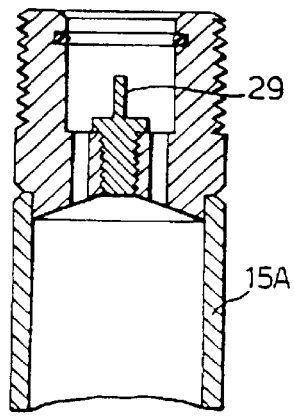
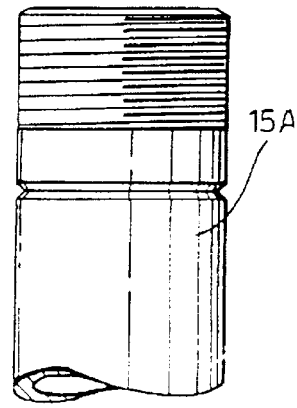

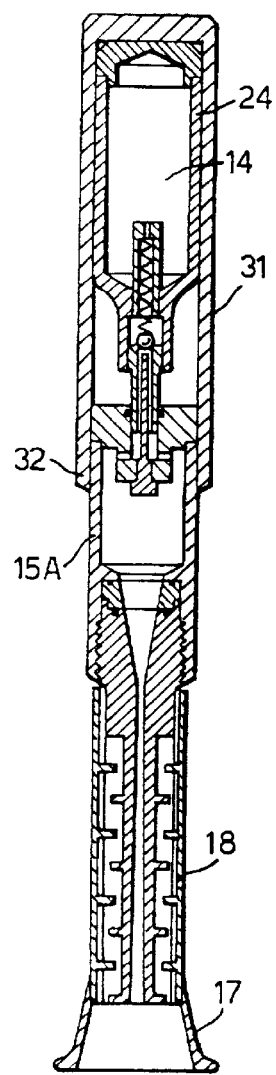
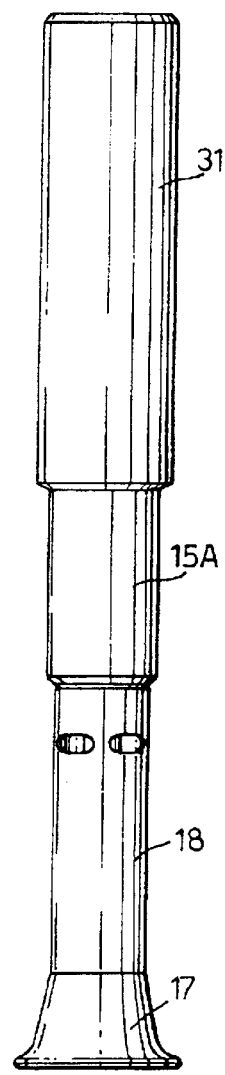

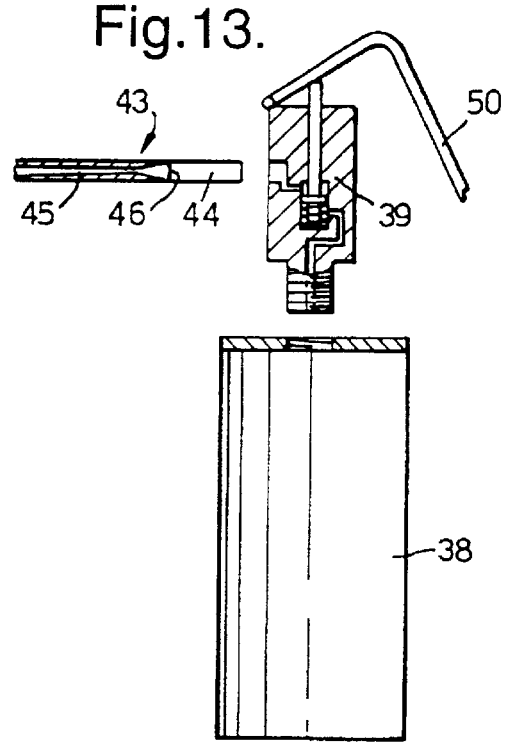
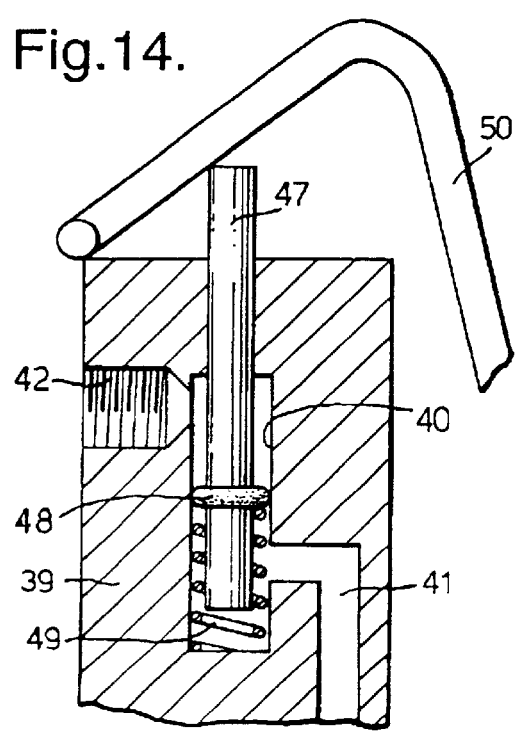

US 7,207,967 B1

PARTICLE DELIVERY

CROSS-REFERENCE TO RELATED APPLICATION

This application is a continuation-in-part of International Patent Application Number PCT/GB95/01948, filed Aug. 17, 1995, designating the United States, from which priority is claimed pursuant to 35 U.S.C. §365(c).

TECHNICAL FIELD

The present invention relates generally to a needleless syringe for use in delivery of particles of a therapeutic agent to a target surface. More particularly, the invention pertains to a needleless syringe system that includes a sealed chamber containing particles of a therapeutic agent and a gas at super-atmospheric pressure.

BACKGROUND OF THE INVENTION

In commonly-owned U.S. application Ser. No. 08/474,367, a non-invasive delivery system is described that entails the use of a needleless syringe. The syringe is used for transdermal delivery of powdered therapeutic compounds and compositions to skin, muscle, blood or lymph. The syringe can also be used in conjunction with surgery to deliver therapeutics to organ surfaces, solid tumors and/or to surgical cavities (e.g., tumor beds or cavities after tumor resection).

The needleless syringe is constructed as an elongate tubular nozzle, having a rupturable membrane initially closing the passage through the nozzle adjacent to the upstream end of the nozzle. Particles of a powdered therapeutic agent are located adjacent to the membrane. The therapeutic agent is delivered using an energizing means which applies a gaseous pressure to the upstream side of the membrane that is sufficient to burst the membrane, thereby producing a supersonic gas flow through the nozzle in which the particles are entrained.

SUMMARY OF THE INVENTION

Recent studies have shown that, by the appropriate selection of the geometry and Mach number for the nozzle in the needleless syringe described in U.S. application Ser. No. 08/474,367, it is possible to provide a pseudo-steady state, supersonic, two-phase flow through the nozzle. Particles that are disposed within this multi-phasic flow travel with a velocity close to that of the propelling gas in which they are entrained. The selected geometry for the nozzle preferably has a convergent upstream portion, leading through a throat to a cylindrical or, preferably, divergent downstream portion.

Consequently, a large proportion of the particles containing the therapeutic agent reach the target under quasi-steady flow conditions and only a small proportion are delivered in transient flow and carried on the contact surface. This leads to considerable benefit both in control and in increased skin or other target penetration and is surprising in such a transient phenomenon. High speed photography of the gas/particle jet has confirmed the quasi-steady flow conditions. Typical photographs of the jet show the jet lasting for 1.5 milliseconds, with reasonably homogenous distribution of the particles throughout the jet. The length of time that the jet lasts allows one to calculate the effective length of the jet and hence its volume. Thus, one is able to conclude that the particles containing the therapeutic agent are arriving in a continuous flow at the target skin or mucosal surface, and, on average, succeeding particles will penetrate in the same holes as preceding particles, reducing damage and trauma to the skin.

This understanding has led to the appreciation that the dose delivered by the needleless syringe delivery system may advantageously be mixed with the driving gas in the gas canister. The delivery system can then be considerably simplified as a rupturable membrane may, in most cases, no longer be needed. In particular, the outlet from the chamber may lead directly to the nozzle via a valve or other means for releasing the gas. This differentiates the invention from previous devices, such as those described in EPA-0535005, which generally rely upon the impact of a shock wave to accelerate particles toward a target surface, whereas the present invention accelerates particles toward a target surface within a flow of gas.

In accordance with the invention, a needleless syringe is constructed as an elongate nozzle, at the upstream end of which is provided a sealed chamber containing gas at superatmospheric pressure and particles of a therapeutic agent. A means is provided for rapidly opening an outlet from the chamber to release the driving gas in a flow, allowing particles of the therapeutic agent, entrained within the gas flow, to exit the chamber and pass through the nozzle with a velocity approaching the supersonic speeds of the driving gas flow. Locating particles of the therapeutic agent within the chamber, which also contains the driving gas under high pressure, considerably simplifies the construction, assembly, and use, of the present needleless syringe.

The outlet from the chamber may incorporate a pierceable membrane or a valve, such as a spring-loaded ball valve, which is actuated by either mechanical means or by manual manipulation, for example, by movement of two parts of the syringe relative to each other.

The chamber may contain a single dose of particles, and hence sufficient gas for delivery of a single administration of a therapeutic agent. Alternatively, the outlet from the chamber may incorporate a valve which can be opened and closed a consecutive number of times to deliver a succession of doses of therapeutic agent. The time during which the valve is opened may be automatically controlled by control means, for example, means entailing the combination of a solenoid or stepping motor to actuate the valve into an open position for successively longer periods to deliver equal doses of therapeutic agent in spite of the successively reducing pressure in the chamber. It will then be appreciated that by placing the therapeutic agent and driving gas within the chamber, creating a homogeneous mixing and suspension of the powdered therapeutic agent, and by using a fast opening metering valve at the exit of the chamber, a multi-shot syringe can be provided which dispenses an infinitely variable, rather than a fixed unit, dosage of the agent. By combining the metering valve with a timing device, the duration of time that the valve is open for each administration may be controlled. The timer can also be adjusted to take account of the desired dose of the therapeutic agent, the gas pressure in the reservoir, and the agent concentration within the reservoir, both of which will decrease with each successive administration. If the initial values of the mass of therapeutic agent, and the gas pressure in the chamber, are known, the required duration of each subsequent administration can be calculated, e.g., by a microprocessor, and the timer adjusted accordingly.

When the actual dose is not critical, for example when the therapeutic agent is an analgesic, the valve may be opened and closed manually. A degree of control may then be provided by means of a rupturable membrane between the valve and the nozzle, the valve being opened to release sufficient gas and particles of therapeutic agent into a rupture chamber upstream of the membrane until the pressure across the membrane has built up sufficiently for the membrane to rupture, whereafter the particles, entrained in the gas, are free to flow from the rupture chamber through the nozzle to the target surface. Upon hearing the membrane burst, the operator of the device can close the valve, for example, by releasing a trigger which holds the valve open against a tensioning means, such as spring pressure.

Sealed chambers, which contain a driving gas under pressure and particles of a selected therapeutic agent, can be supplied as a separate unit from the rest of the needleless syringe device. At the time of use, a sealed chamber is attached to the syringe which includes the tubular nozzle, and, possibly, a diaphragm-piercing or valve-opening means.

One slight disadvantage with the needleless syringe described in U.S. application Ser. No. 08/474,367, wherein gas pressure is used to burst the rupturable membrane, is the possibility of having less than the entire prescribed dose of particles of the therapeutic agent delivered within the gas flow, for example, if a portion of the particles are retained in the proximity of the remnants of the burst membrane. With the present invention, this disadvantage can be overcome if the particles are initially located in one or more open ended passageways within the chamber, and arranged such that upon opening of the outlet and release of the compressed gas, at least some of this gas sweeps through the passageway(s) and thus entrains substantially all the particles within the passageway(s). The particles may be initially retained in the passageways under gravity, electrostatically, or by means of weak membranes closing the ends of the passageways until ruptured by the release of pressure.

Another embodiment entails the provision of very small particles of a powdered therapeutic agent which are small enough to remain suspended in the gas for a few seconds when agitated, but big enough to prevent their direct entry into cells in the targeted surface, thereby reducing the bio-availability of the agent. In this regard, it is preferred that the particles of the therapeutic agent delivered with the present devices occupy extra-cellular space and hence diffuse readily into the systemic circulation. Particle diameters of between 10–20 µm are preferable. A ball bearing may be placed inside the gas canister to help provide a homogenous distribution of the particles of the therapeutic agent upon shaking, prior to their administration.

Study of the jet released from the present devices, and its arrival at the target surface, has further led to the appreciation that the jet dimensions are important and affect the concentration of therapeutic agent delivered per unit volume of target skin or mucosa. By increasing the volume of the driving gas, one may lengthen the duration of the jet and increase the dosage of agent that is delivered, subject to limitations particular to the selected therapeutic agent. For a given concentration, delivered dosages may also be increased by increasing the targeted surface area. This can be achieved by increasing the diameter of the throat of the nozzle, while maintaining the ratio of inlet and exit diameters constant. Target diameter may also be increased by increasing the spacing distance of the nozzle exit from the target.

Reference is made to U.S. application Ser. No. 08/474,367 for other aspects of the needleless syringe, for example, the use of a spacer/silencer at the downstream end of the nozzle, various alternative nozzle geometries, types of therapeutic agent particles which may be delivered, and the composition, and pressure, of the driving gas to be used.

BRIEF DESCRIPTION OF THE FIGURES

Some examples of syringes constructed in accordance with the present invention are illustrated diagrammatically in the accompanying drawings, in which:

FIG. 1 is an axial section through a first embodiment of the invention;

FIG. 2 is a side elevation of the embodiment of FIG. 1;

FIGS. 5 and 6 are exploded views of portions of the second embodiment of the invention depicted in FIGS. 3 and 4;

FIGS. 7 and 8 show an alternative embodiment of the device of FIGS. 3–6;

FIGS. 9 and 10 show yet another alternative embodiment of the device depicted in FIGS. 3–6;

FIG. 13 is an exploded view of a third embodiment of the invention;

FIG. 14 is an enlarged view of a portion of the device of FIG. 13; and,

DETAILED DESCRIPTION OF THE PREFERRED EMBODIMENTS

Figure 3:
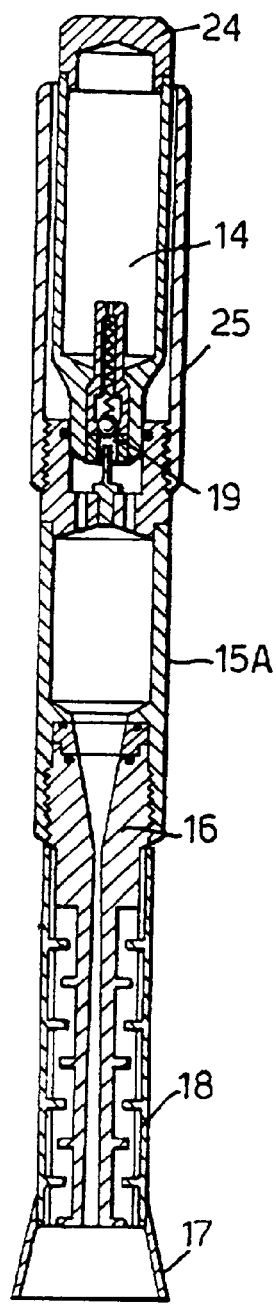
FIGS. 3 and 4 correspond to FIGS. 1 and 2, showing a second embodiment of the invention.
Figure 4:
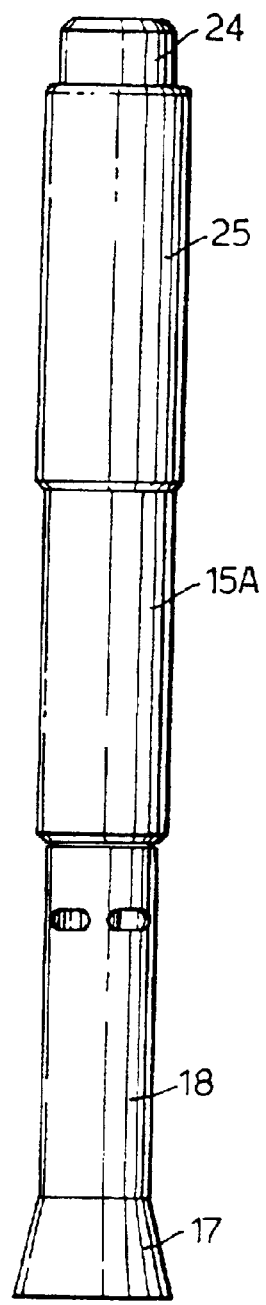

Before describing the present invention in detail, it is to be understood that this invention is not limited to particular pharmaceutical formulations or process parameters as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "a therapeutic agent" includes a mixture of two or more such agents, reference to "a gas" includes mixtures of two or more gases, and the like.

A. Definitions

Unless defined otherwise, all technical and scientific terms used herein have the same meaning as commonly understood by one of ordinary skill in the art to which the invention pertains. The following terms are intended to be defined as indicated below.

The term "transdermal" delivery captures both transdermal (or "percutaneous") and transmucosal administration, i.e., delivery by passage of a therapeutic agent through the skin or mucosal tissue. See, e.g., *Transdermal Drug Delivery: Developmental Issues and Research Initiatives*, Hadgraft and Guy (eds.), Marcel Dekker, Inc., (1989); *Controlled Drug Delivery: Fundamentals and Applications*, Robinson and Lee (eds.), Marcel Dekker Inc., (1987); and

*Transdermal Delivery of Drugs*, Vols. 1–3, Kydonieus and Berner (eds.), CRC Press, (1987). Aspects of the invention which are described herein in the context of "transdermal" delivery, unless otherwise specified, are meant to apply to both transdermal and transmucosal delivery. That is, the compositions, systems, and methods of the invention, unless explicitly stated otherwise, should be presumed to be equally applicable to transdermal and transmucosal modes of delivery.

As used herein, the terms "therapeutic agent" and/or "particles of a therapeutic agent" intend any compound or composition of matter which, when administered to an organism (human or animal) induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. More particularly, the term "therapeutic agent" includes compounds or compositions for use in all of the major therapeutic areas including, but not limited to, anti-infectives such as antibiotics and antiviral agents; analgesics and analgesic combinations; local and general anesthetics; anorexics; antiarthritics; antiasthmatic agents; anticonvulsants; antidepressants; antihistamines; anti-inflammatory agents; antinauseants; antineoplastics; antipruritics; antipsychotics; antipyretics; antispasmodics; cardiovascular preparations (including calcium channel blockers, beta-blockers, beta-agonists and antiarythmics); antihypertensives; diuretics; vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins peptides and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like).

Particles of a therapeutic agent, alone or in combination with other drugs or agents, are typically prepared as pharmaceutical compositions which can contain one or more added materials such as carriers, vehicles, and/or excipients. "Carriers," "vehicles" and "excipients" generally refer to substantially inert materials which are nontoxic and do not interact with other components of the composition in a deleterious manner. These materials can be used to increase the amount of solids in particulate pharmaceutical compositions. Examples of suitable carriers include water, silicone, gelatin, waxes, and like materials. Examples of normally employed "excipients," include pharmaceutical grades of dextrose, sucrose, lactose, trehalose, mannitol, sorbitol, inositol, dextran, starch, cellulose, sodium or calcium phosphates, calcium sulfate, citric acid, tartaric acid, glycine, high molecular weight polyethylene glycols (PEG), and combinations thereof. In addition, it may be desirable to include a charged lipid and/or detergent in the pharmaceutical compositions. Such materials can be used as stabilizers, anti-oxidants, or used to reduce the possibility of local irritation at the site of administration. Suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics, Danbury, Conn.), polyoxyethylenesorbitans, e.g., TWEEN® surfactants (Atlas Chemical Industries, Wilmington, Del.), polyoxyethylene ethers, e.g., Brij, pharmaceutically acceptable fatty acid esters, e.g., lauryl sulfate and salts thereof (SDS), and like materials.

"Gene delivery" refers to methods or systems for reliably inserting foreign nucleotide sequences, either DNA or RNA, into host cells. Such methods can result in expression of non-integrated transferred nucleotide sequences, extrachromosomal replication and expression of transferred replicons (e.g., episomes), or integration of transferred genetic material into the genomic DNA of host cells.

By "vector" is meant any genetic element, such as a plasmid, phage, transposon, cosmid, chromosome, virus, virion, etc., which is capable of replication when associated with the proper control elements and which can transfer gene sequences between cells.

B. General Methods

One embodiment of the needleless syringe of the present invention is shown in FIGS. 1 and 2. The needleless syringe has an upper barrel portion 13 containing a sealed reservoir or chamber 14. The barrel portion 13 is coupled via a lower barrel portion 15 to a nozzle 16 which can be associated with a spacer 17 and silencer 18. The barrel portion 13 can be coupled to the lower barrel portion by screw threads, or the like. An outlet 19 in the bottom of the chamber 14 is in communication with a release means 20, which is arranged at a chamber-nozzle interface. The release means 20 can comprise any suitable element, such as a valve or the like, which is capable of controlling communication between the chamber 14 and the nozzle 16 via the lower barrel portion 15. The release means can be actuated between open and closed positions by any suitable means, for example, by the action of a plunger 21 which is depressible by a button 22. In the embodiment depicted in FIGS. 1–2, the release means 20 comprises a valve.

Particles 23 of a powdered therapeutic agent are located within the chamber 14. When the particles are to be delivered to a target surface, the button 22 is depressed to move a sealed carrying part of the valve downwardly and out of the outlet 19 to actuate the valve into an open position. Opening of the valve releases the compressed gas in a supersonic gas flow, wherein the gas flow contains particles from the chamber 14 which pass through the nozzle 16 for delivery to a target surface positioned beyond the spacer 17.

The syringe shown in FIGS. 3–6 differs from the embodiment of FIGS. 1 and 2 in that the chamber 14 is provided by a canister 24 which is slidable within a sleeve 25 corresponding to the upper barrel portion 13 in the first example. An outlet 19A is closed by a valve which can be actuated between open and closed positions to allow or prevent the passage of the contents of chamber 14 to other, downstream, portions of the needleless syringe. In the particular embodiment depicted in FIGS. 3 and 4, the valve is actuated by a ball closure element 26 which is urged onto a seating 27 by a helically coiled compression spring 28. Within a lower barrel portion 15A of the syringe, there is provided a projection 29 which is sized to enter the outlet 19A. When the upper end of the canister 24 is pressed downwardly into the upper barrel portion 25, the projection 29 serves to displace the ball closure element 26 from its seat, thereby allowing sudden release of gas and particles contained within the chamber 14. The valve may be reclosed, for example, when the syringe is used for multiple administrations of a therapeutic agent from the chamber, by releasing the pressure applied to the upper end of the canister and allowing the ball closure to return to it's seated position.

Another embodiment of the invention is shown in FIGS. 7 and 8. This embodiment is substantially similar to the device depicted in FIGS. 3 to 6; however, the ball closure element 26 is moved between open and closed positions by movement of a thumb piece 68 that is pivotally mounted in the top of the barrel portion 25. More particularly, the thumb piece 68 is mounted by means of a lug which engages an aperture 30 in the barrel portion of the syringe device. Depression of the thumb piece forces the canister 24 downwards within the sleeve 25, thereby providing a mechanical advantage which facilitates movement of the ball closure element 26 against the high pressure within the chamber 14 to displace it from its seat, allowing release of the gas and particles contained within the chamber 14.

The ball closure element 26 can also be actuated by way of a modified housing. Referring now to FIGS. 9 and 10, an alternative means for urging the canister 24 downwardly in the syringe to open the ball valve is shown. In this example a cylindrical shroud 31 fits over the canister 24. The shroud is constructed to slide relative to the rest of the syringe such that an open lower end 32 of the shroud slides over the lower barrel portion 15A. Downward pressure on the closed upper end of the shroud 31 forces the canister 24 downwards to open the valve.

Figure 11:
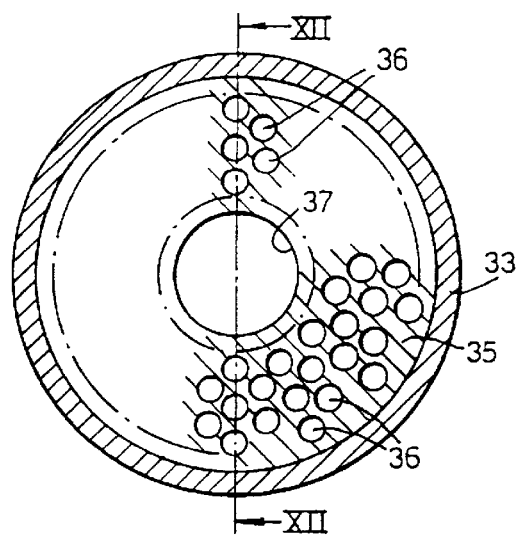
FIG. 11 is a diagrammatic axial view of a canister for use with the devices of the invention.
Figure 12:
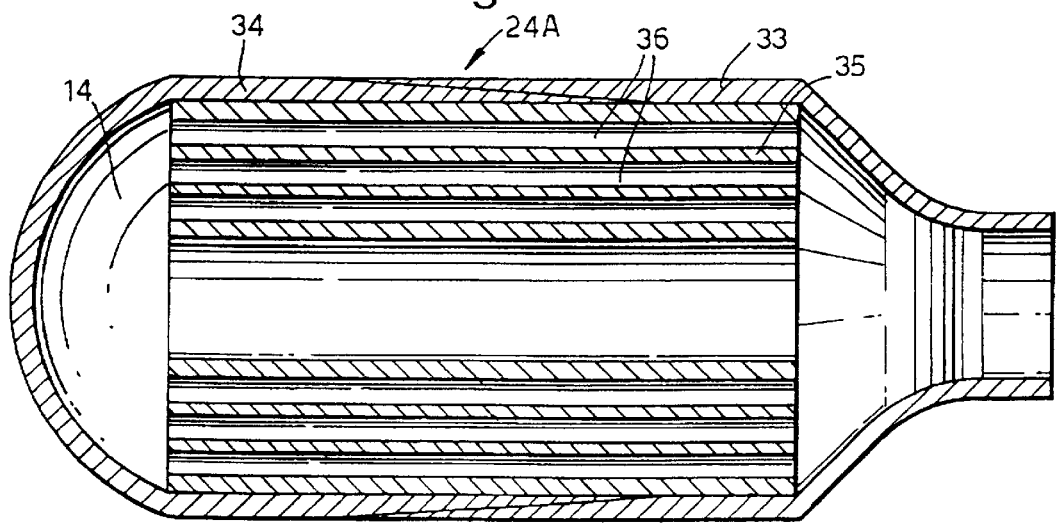
FIG. 12 is a section taken along XII—XII in FIG. 11.

The pressure containing parts of the syringe will usually be made of metal, but may also be made of a rigid engineering polymeric material, for example, a polycarbonate. A canister 24A made of such a polymeric material is shown in FIGS. 11 and 12. The body of the canister is made in two parts 33 and 34 which are fused or welded together. The canister contains an insert 35 consisting of a number of substantially parallel cylindrical passageways 36. Upon assembly, the canister is filled with high pressure gas and the particles of therapeutic agent are located within the passageways 36. An outlet 37 of the canister may be fitted with a ball valve such as in the previous examples, or closed by means of a pierceable diaphragm which is sufficiently strong to contain the internal gas pressure but which may be readily breached by a needle, which may be hollow, when the canister is moved relative to the needle.

A number of alternative canister configurations can be used with the present needleless syringes without departing from the spirit of the invention. For example, alternative canister configurations can be provided having means for disaggregating particles of the therapeutic agent to provide a more homogenous suspension of particles within the released gas flow. Any irregular interior surface feature within the canisters 24 and/or 24A can be used in this manner to agitate and/or disaggregate particles as they exit the canister. Such features include, but are not limited to, one or more baffles, retaining tubes, or like structures, formed on the interior surface of the canister. In the alternative, a series of features can be used to force the gas and particles along a tortuous path when exiting the canister. For example, a helical or otherwise spiral feature can be used to impart a spin on the exiting gas and particles as they exit the canister. Also, a moveable feature, such as a propeller, can be arranged adjacent to the outlet 37 of the canister. As the exiting gas flows through the outlet, the propeller blades are caused to spin, thereby helping to disaggregate particles contained within the gas flow.

The canisters 24 and/or 24A can also have a sealing membrane arranged over the outlet 37. The membrane can be used to maintain a sterile barrier about the outlet, such as in applications where the canisters are handled separately from the rest of the syringe up until the time the therapeutic agent is to be delivered.

In another embodiment of the invention, a needleless syringe is provided that is capable of delivering multiple doses of a therapeutic agent. Referring now to FIGS. 13 and 14, a multi-dose syringe is shown which comprises a canister 38, containing compressed gas, particles of therapeutic agent, and an agitator, such as a metal ball. Prior to discharge, the canister is shaken so that the particles are suspended in the gas and entrained by the gas when it is released.

Attached to the lid of the canister is a valve housing, generally indicated at 39, that contains a valve chamber having a lower side passage 41 which communicates with the canister 38 into which it opens, and an upper side passage 42 to which is attached a nozzle assembly 43. The nozzle assembly comprises a rupture chamber 44 and a nozzle 45 separated by a rupturable membrane 46. The assembly further includes a plunger 47, that extends into the valve chamber 40. A sealing O-ring 48, arranged adjacent to one end of the plunger maintains a seal between the plunger and the walls of the valve chamber 40. The plunger is urged upwardly by a compression spring 49 so that the O-ring 48 is maintained above the side passage 41.

In order to actuate the device, the plunger 47 is depressed against the action of the compression spring 49 by the downward displacement of an L-shaped lever 50, which is pivotally connected to the valve housing 39. The downward displacement of the lever causes the O-ring 48 to move below the passage 41, thereby allowing release of a suspension of particles of the therapeutic agent and conveying gas from the canister 38 into the rupture chamber 44. When the pressure in the chamber 44 has built up sufficiently, the membrane 46 bursts and the particles, entrained in a supersonic gas flow, are ejected toward a target surface through the nozzle 45. The lever 50 can be manipulated by grasping the canister 38 in the palm of an operator's hand, and depressing the free end of the lever. As soon as the operator hears the membrane burst, the lever 50 can be released, so that the plunger 47 is returned to its closed position under the action of the spring 49, effectively reclosing the valve. Before the next injection is delivered from the device, the membrane 46 can be replaced, for example by detaching the nozzle 45 from the nozzle assembly 43 to access the membrane.

Figure 15:
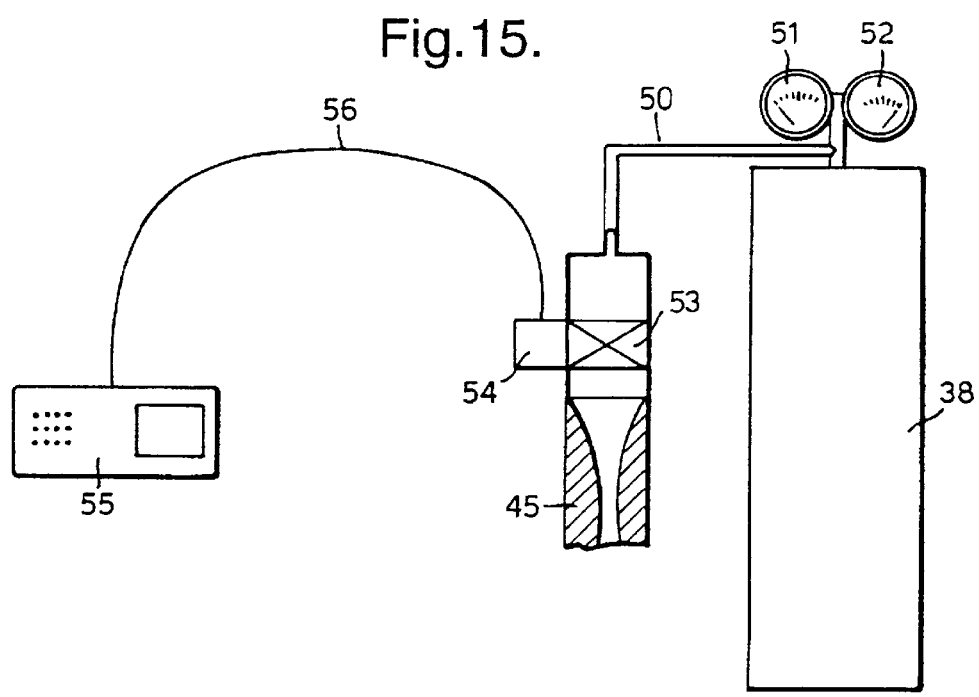
FIG. 15 is a pictorial representation of a still further embodiment of the invention.

Referring now to FIG. 15, another multidose needleless syringe system is shown. The system shown in FIG. 15 differs from the system of FIGS. 13 and 14 in that the canister 38, which contains the driving gas and the particles of the therapeutic agent, is not directly attached to the nozzle 45. Instead, an assembly comprising the nozzle communicates with the canister via a canister-nozzle interface, which can include tubing 50, which may be rigid or flexible. In the embodiment of FIG. 15, the interface also includes a pressure regulator 51, a pressure indicator 52, and a control valve 53, which are respectively used to regulate a desired pressure within the system, and to deliver doses of the therapeutic agent from the canister 38. The valve can be any suitable fast acting valve, and is generally controlled by a solenoid or stepping motor 54 which can be under the control of a micro-processor 55. In the particular embodiment depicted in FIG. 15, the micro-processor is connected to the control 54 by an umbilical 56. In this example the valve 53 is opened for a predetermined time according to a timing program supplied by the micro-processor 55, thereby allowing a selected dose of the therapeutic agent to be ejected through the nozzle 45. The micro-processor can be programmed with dosage parameters, such as information regarding one or more desired dosages, the initial pressure of gas contained within the canister 38 and the original concentration of the particles of therapeutic agent within the gas. In this manner, a selected dose can be repeatedly delivered from the device, irrespective of a concomitant reduction in the gas pressure within the canister 38.

Typically, in each of the illustrated examples, the gas provided in the chamber 14, or within the canisters 24, 24A, or 38, may be helium at a pressure of the order of 40 to 80 bar. However, any other suitable delivery gas may be used. The nozzles 16 or 45 may be of convergent/divergent, or convergent/cylindrical form with a length of between 50 and 100 mm, preferably 60 mm, and a throat diameter of between 1 and 10 mm, preferably between 1.5 and 5 mm.

The needleless syringes of the present invention can be used for transdermal delivery of powdered therapeutic compounds and compositions, for delivery of genetic material into living cells (e.g., gene therapy or nucleic acid vaccination), both in vivo and ex vivo, and for the delivery of biopharmaceuticals to skin, muscle, blood or lymph. The syringes can also be used in conjunction with surgery to deliver therapeutic agents, drugs, immunogens, and/or biologics to organ surfaces, solid tumors and/or to surgical cavities (e.g., tumor beds or cavities after tumor resection). In theory, practically any agent that can be prepared in a substantially solid, particulate form can be safely and easily delivered using the present devices.

Delivery of therapeutic agents from the above-described needleless syringe systems is practiced with particles having an approximate size generally ranging from 0.1 to 250 μm. For drug delivery, the optimal particle size is usually at least about 10 to 15 μm (the size of a typical cell). For gene delivery, the optimal particle size is generally substantially smaller than 10 μm. Particles larger than about 250 μm can also be delivered from the devices, with the upper limitation being the point at which the size of the particles would cause untoward damage to the skin cells. The actual distance which the delivered particles will penetrate a target surface depends upon particle size (e.g., the nominal particle diameter assuming a roughly spherical particle geometry), particle density, the initial velocity at which the particle impacts the surface, and the density and kinematic viscosity of the targeted skin or mucosal tissue. In this regard, optimal particle densities for use in needleless injection generally range between about 0.1 and 25 $g/cm^3$, preferably between about 0.9 and 1.5 $g/cm^3$, and injection velocities generally range between about 200 and 3,000 m/sec. With appropriate gas pressure, particles of a therapeutic agent having an average diameter of 10–70 μm are accelerated through the nozzle at velocities approaching the supersonic speeds of the driving gas flow.

Accordingly, novel needleless syringe delivery systems and methods for using the same are disclosed. Although preferred embodiments of the subject invention have been described in some detail, it is understood that obvious variations can be made without departing from the spirit and the scope of the invention as defined by the appended claims.

What is claimed is:

1. A needleless syringe, comprising:
   (a) an elongate nozzle having an upstream end;
   (b) a sealed chamber connected to the upstream end of the nozzle to provide a chamber-nozzle interface, said chamber having an outlet in communication with the chamber-nozzle interface and containing gas at super-atmospheric pressure and particles of a therapeutic agent; and
   (c) release means positioned at the chamber-nozzle interface and closing off the outlet, wherein said release means can be actuated to open the outlet and release a supersonic gas flow from the chamber into the nozzle, wherein said gas flow contains particles of the therapeutic agent entrained therein which pass through the nozzle for delivery to a target surface.

2. The syringe of claim 1, wherein a membrane is disposed over the chamber outlet.

3. The syringe of claim 1, wherein the release means comprises a valve.

4. The syringe of claim 3, wherein the valve can be actuated between open and closed positions to open and close the outlet and thereby deliver a succession of doses of the therapeutic agent from the chamber.

5. The syringe of claim 4, wherein the valve is actuated to an open position for a set period of time by an associated control means.

6. The syringe of claims 5, wherein the control means successively actuates the valve to an open position for a predetermined number of time periods.

7. The syringe of claim 6, wherein the time periods in which the valve is open are successively longer, thereby delivering substantially equivalent doses of the therapeutic agent from the chamber despite a concomitant reduction of gas pressure in the chamber as a result of each previous delivery.

8. The syringe of claim 5, wherein the control means comprises a solenoid or a stepping motor which is operably connected to said valve and moves said valve between open and closed positions.

9. The syringe of claim 1, wherein the chamber comprises an interior surface having one or more internal features arranged thereon such that the gas flow passes by or through said features and entrains particles of the therapeutic agent therein upon release from the chamber.

10. The syringe of claim 9, wherein the internal features comprise one or more open-ended passageways that extend through an insert which is positioned within the chamber.

11. A needleless syringe, comprising:
   (a) an elongate nozzle having an upstream end;
   (b) a chamber connected to the upstream end of the nozzle to provide a chamber-nozzle interface;
   (c) a sealed canister disposed within the chamber, said canister having an outlet for communicating with the chamber-nozzle interface, wherein said canister contains gas at super-atmospheric pressure and particles of a therapeutic agent; and
   (d) release means closing off the outlet, wherein said release means can be actuated to open the outlet and release a supersonic gas flow from the canister into the nozzle, wherein said gas flow contains particles of the therapeutic agent entrained therein which pass through the nozzle for delivery to a target surface.

12. The syringe of claim 11, wherein the release means comprises a valve.

13. The syringe of claim 12, wherein the valve can be actuated between open and closed positions to open and close the outlet and thereby deliver a succession of doses of the therapeutic agent from the cannister.

14. The syringe of claim 13, wherein the valve is actuated to an open position for a period of time by an associated control means.

15. The syringe of claim 14, wherein the control means successively actuates the valve to an open position for a predetermined number of time periods.

16. The syringe of claim 15, wherein the time periods in which the valve is open are successively longer, thereby delivering substantially equivalent doses of the therapeutic agent from the canister despite a concomitant reduction of gas pressure in the canister as a result of each previous delivery.

17. The syringe of claim 14, wherein the control means comprises a solenoid or a stepping motor which is operably connected to said valve and moves said valve between open and closed positions.

18. The syringe of claim 11, wherein the canister comprises an interior surface having one or more internal features arranged thereon such that the gas flow passes by or through said features and entrains particles of the therapeutic agent therein upon release from the canister.

19. The syringe of claim 18, wherein the internal features comprise more or more open-ended passageways that extend through an insert which is positioned within the canister.

20. A needleless syringe, comprising:

(a) an elongate nozzle having an upstream end;

(b) a sealed canister connected to the upstream end of the nozzle by means of a canister-nozzle interface, said canister containing gas at super-atmospheric pressure and particles of a therapeutic agent; and (c) release means positioned within the canister-nozzle interface which can be actuated to release a supersonic gas flow from the canister, wherein said gas flow contains particles of the therapeutic agent entrained therein which pass through the nozzle for delivery to a target surface.

21. The syringe of claim 20, wherein the canister-nozzle interface further comprises tubing that connects the canister with the upstream end of the nozzle.

22. The syringe of claim 3, wherein the valve is actuated by movement of two parts of the syringe relative to each other.

23. The syringe of claim 22, wherein the valve is actuated by movement of the sealed chamber towards the upstream end of the nozzle.

24. The syringe of claim 12, wherein the valve is actuated by movement of two parts of the syringe relative to each other.

25. The syringe of claim 24, wherein the valve is actuated by movement of the sealed chamber towards the upstream end of the nozzle.

26. The syringe of claim 1, wherein the therapeutic agent is a drug.

27. The syringe of claim 1, wherein the therapeutic agent is a vaccine.

* * * * *